(12) United States Patent
Siochi

(10) Patent No.: US 6,813,336 B1
(45) Date of Patent: Nov. 2, 2004

(54) HIGH DEFINITION CONFORMAL ARC RADIATION THERAPY WITH A MULTI-LEAF COLLIMATOR

(75) Inventor: Ramon Alfredo Carvalho Siochi, Apex, NC (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 60 days.

(21) Appl. No.: 09/642,183

(22) Filed: Aug. 17, 2000

(51) Int. Cl.$^7$ .................................................. A61N 5/10
(52) U.S. Cl. ........................ 378/65; 378/64; 378/147; 378/153
(58) Field of Search ...................... 378/65, 64, 147, 378/160, 153, 152

(56) References Cited

U.S. PATENT DOCUMENTS

| | | | |
|---|---|---|---|
| 5,216,255 A | | 6/1993 | Weidlich ................ 250/492.3 |
| 5,663,999 A | | 9/1997 | Siochi ........................ 378/65 |
| 5,724,403 A | | 3/1998 | Siochi et al. ............... 378/150 |
| 5,748,703 A | * | 5/1998 | Cosman ...................... 378/152 |
| 5,818,902 A | * | 10/1998 | Yu ............................. 378/65 |
| 6,134,296 A | * | 10/2000 | Siochi ........................ 378/65 |
| 6,314,159 B1 | * | 11/2001 | Siochi ........................ 378/65 |
| 6,330,300 B1 | * | 12/2001 | Siochi ........................ 378/65 |
| 6,449,335 B1 | * | 9/2002 | Siochi ........................ 378/65 |

FOREIGN PATENT DOCUMENTS

GB 2346057 A 7/2000

* cited by examiner

*Primary Examiner*—David V. Bruce
*Assistant Examiner*—Courtney Thomas (57) ABSTRACT

A method for delivering radiation from radiation source to a treatment area. A multi-leaf collimator is positioned between the radiation source and the treatment area to block a portion of the radiation and to define a first treatment field. The collimator is positioned with leaves of the collimator extending longitudinally in a first direction. The collimator is first moved through an arc while delivering radiation through the first treatment field to the treatment area. The multi-leaf collimator is rotated about a central axis extending generally perpendicular to a plane containing at least a portion of the leaves such that the leaves define a second treatment field. The multi-leaf collimator is then moved through a second arc while delivering radiation through the second treatment field to the treatment area.

15 Claims, 10 Drawing Sheets

HIGH DEFINITION CONFORMAL ARC RADIATION THERAPY WITH A MULTI-LEAF COLLIMATOR

FIELD OF THE INVENTION

The present invention relates generally to a radiation emitting device, and more particularly, to a method and system for delivering radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

Conformal arc therapy uses a multi-leaf collimator attached to the gantry to deliver radiation as the gantry moves through an arc. Conformal arc therapy is typically delivered with a wide-leaf (e.g., 1 cm) multi-leaf collimator. In such intensity modulation, borders between critical structures and tumor volumes are sometimes not well approximated with a standard one centimeter width leaf which provides a one centimeter by one centimeter grid (cell size) over the intensity map. Each leaf can be moved longitudinally towards or away from a central axis of the beam, however, the field conformation is limited since the leaves are fixed in all but one linear direction. This results in critical areas adjacent to the border being exposed to radiation and results in sharp transitions along the border. A higher resolution than typically provided with the one centimeter leaf is often required. One possible solution is to provide a collimator with thinner leaves. However, the additional hardware required for the additional leaves is expensive, adds weight to the system, may reduce clearance between the treatment head and the patient, and may decrease reliability and life of the system.

Another method used with conformal arc therapy replaces the multi-leaf collimator with a block formed from a radiation shielding material (e.g., lead alloy) and having an opening shaped to generally correspond to the treatment area. This requires a separate block to be manufactured for each treatment area so that the opening corresponds to the specific shape of the tumor or other area to be radiated.

Accordingly, there is therefore, a need for a method for achieving higher spatial resolution radiation therapy without changing current multi-leaf collimator leaf widths or using lead alloy blocks specially designed for each radiation treatment.

SUMMARY OF THE INVENTION

A method for delivering radiation from a radiation source to a treatment area utilizing a multi-leaf collimator is disclosed. The method includes positioning a multi-leaf collimator between the radiation source and treatment area to block a portion of the radiation and define a first treatment field. The collimator is positioned with the leaves of the collimator extending longitudinally in a first direction. The method further includes moving the multi-leaf collimator through a first arc while delivering radiation through the first treatment field to the treatment area The multi-leaf collimator is then rotated about a central axis extending generally perpendicular to a plane containing at least a portion of the leaves and the leaves are positioned to define a second treatment field. The method further includes moving the multi-leaf collimator through a second arc while delivering radiation through the second treatment field to the treatment area.

The leaves may also be moved longitudinally after moving the multi-leaf collimator through the arc to define additional treatment fields. In a preferred embodiment, the first and second arcs have the same geometry and the same starting and ending positions.

The method may further include dividing the treatment area into a plurality of cells each having a defined treatment intensity level. The cells are grouped to form a plurality of matrices, each of the matrices having at least one dimension approximately equal to a width of a collimator leaf. Each of the matrices is decomposed into orthogonal matrices which are used to define the treatment field.

In another aspect of the invention, a system for delivering radiation from a radiation source to a treatment area comprises a collimator having multiple leaves for blocking radiation from said source and defining an opening between the radiation source and said treatment area The collimator is operable to move through an arc over the treatment area and rotate about a central axis of a radiation beam emitted from the radiation source. The system further includes a controller configured to position the leaves to define a first treatment field, move the collimator through a first arc while delivering radiation through the first treatment field, rotate the collimator about the central axis, position the leaves to define a second treatment field, and move the collimator through a second arc while delivering radiation through the second treatment field to the treatment area.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
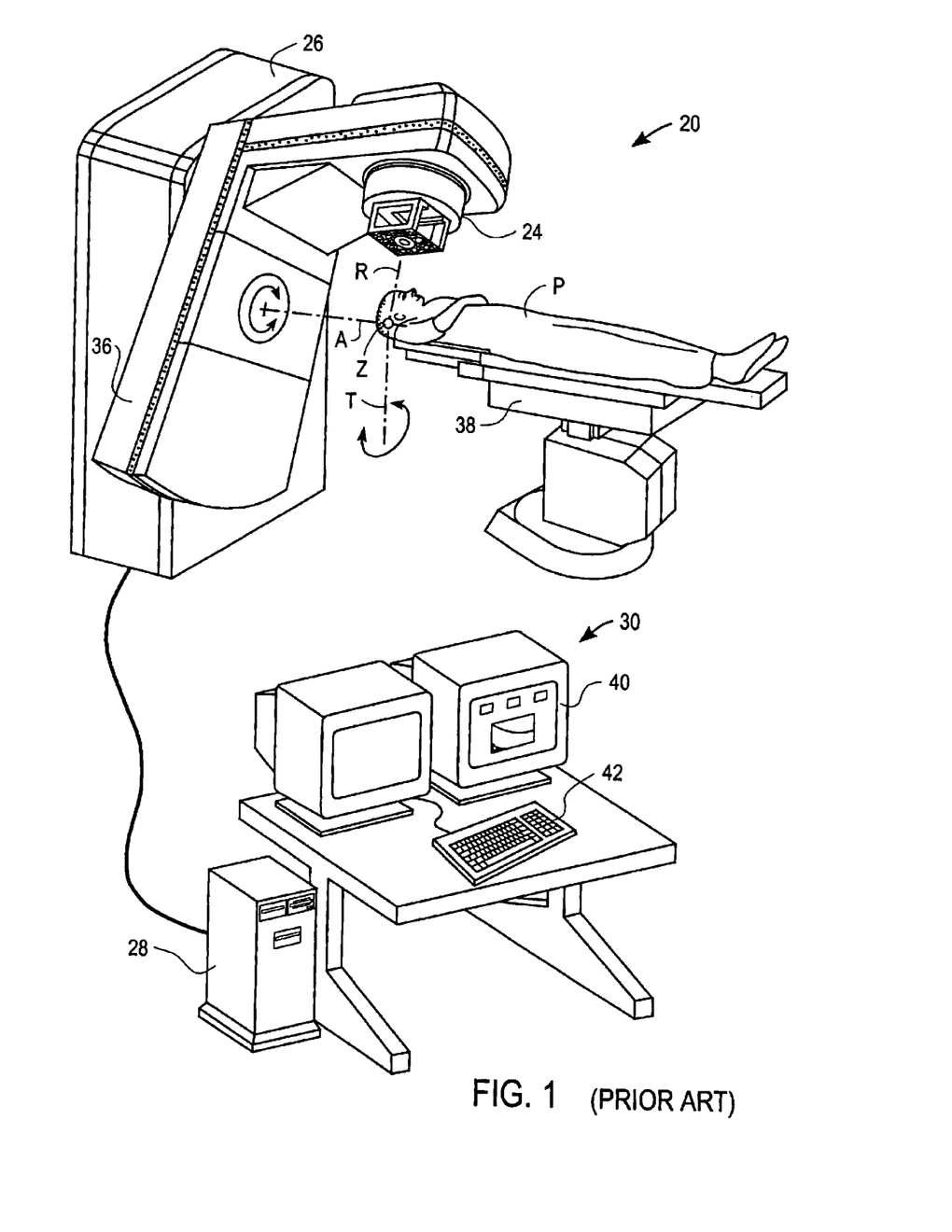
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
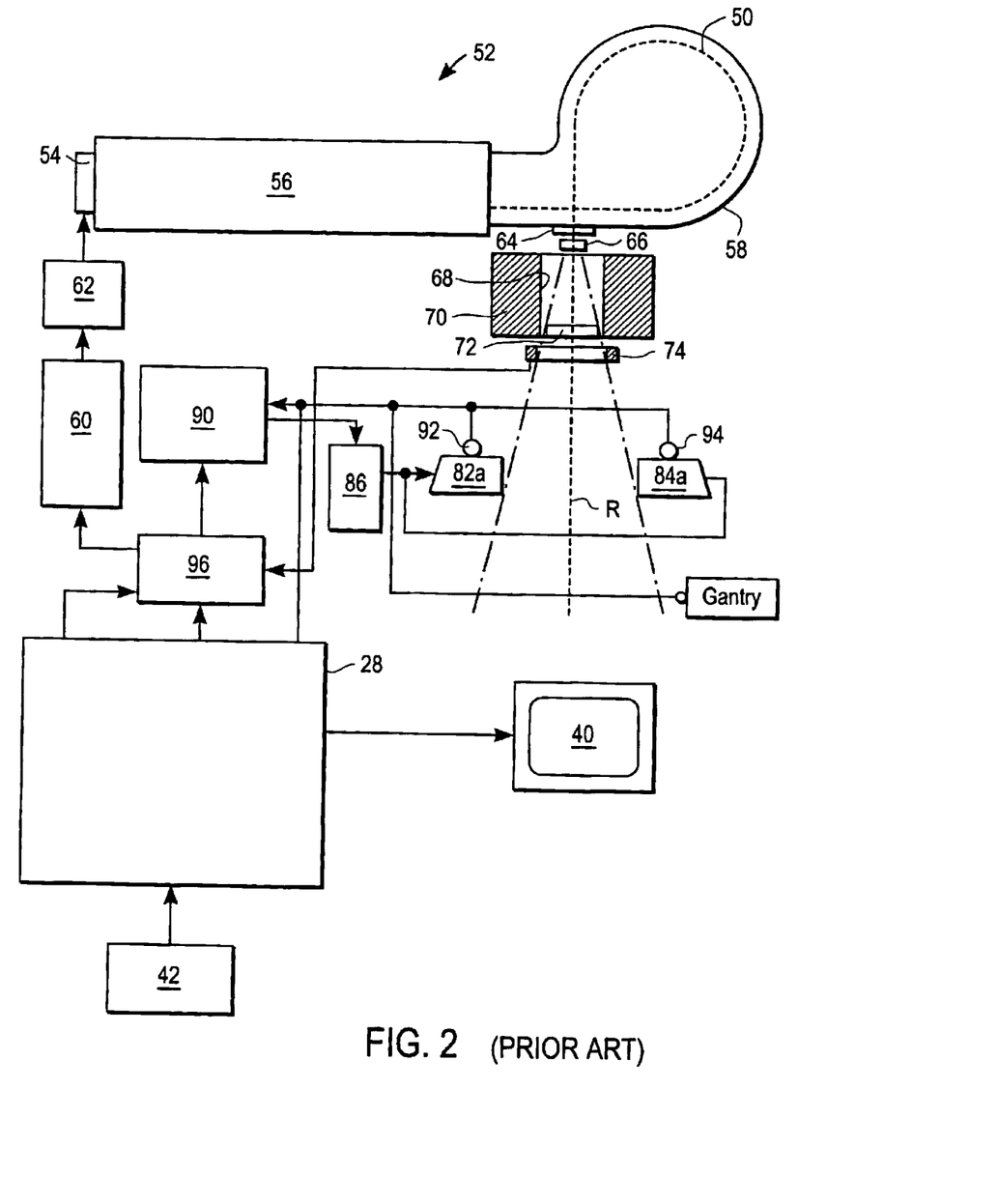
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
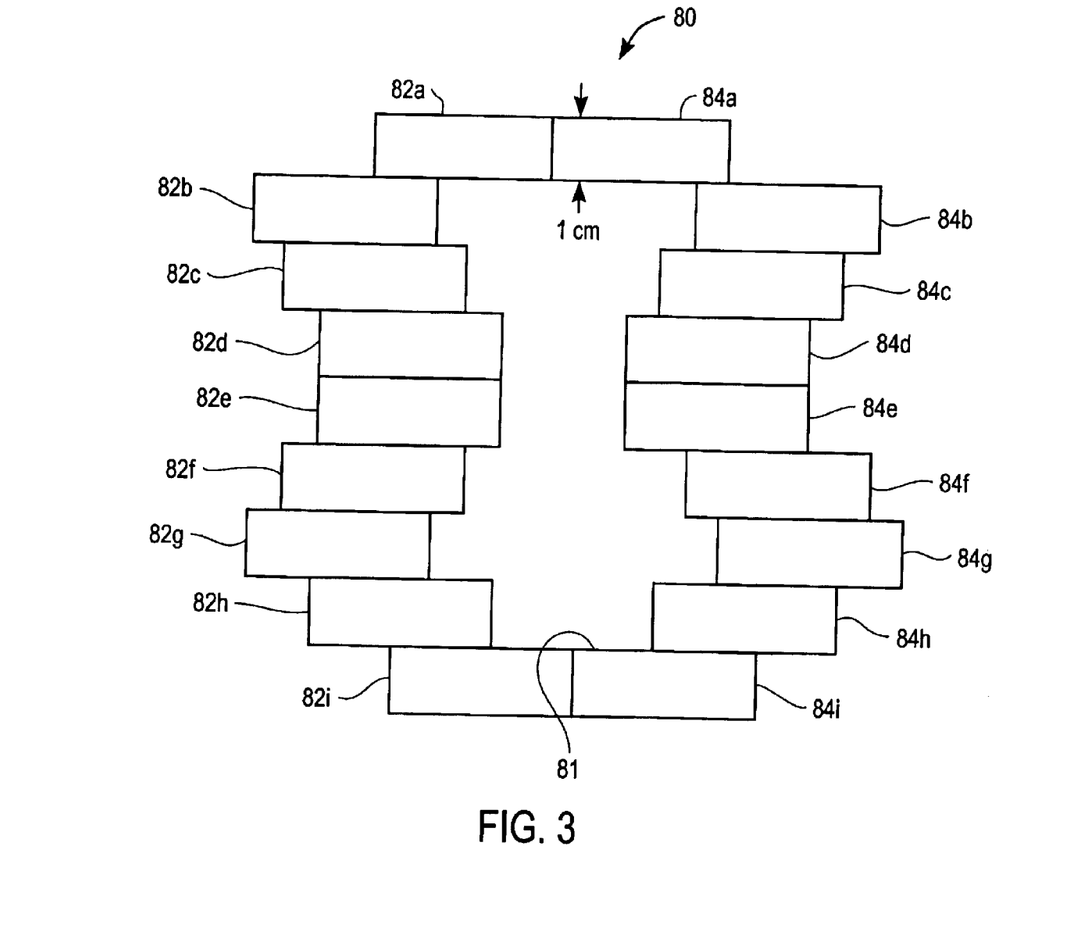
FIG. 3 is a schematic illustrating leaves of a multi-leaf collimator positioned for treatment in the radiation treatment device of FIG. 1.

A beam shielding device, generally indicated at 80, is provided in the path of the beam 50 to define a treatment field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation.

The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the optimization process described below.

Figure 4:
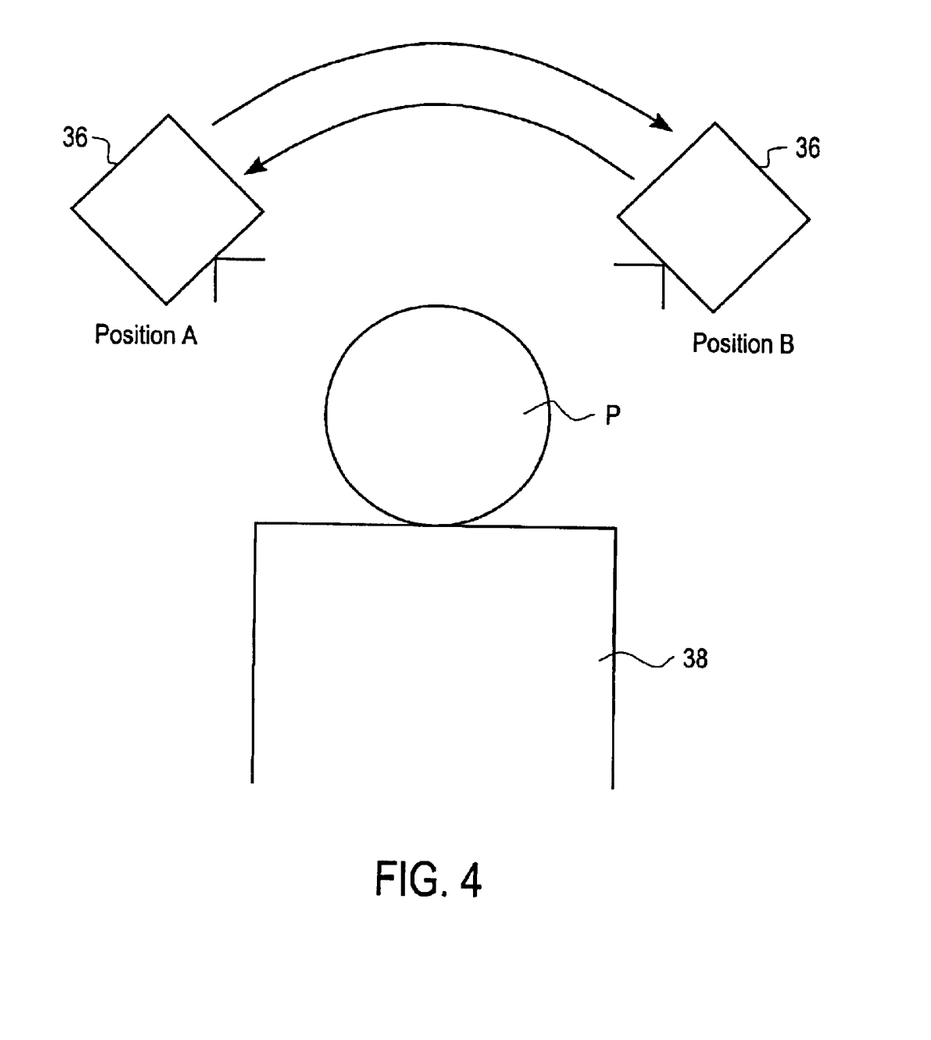
FIG. 4 is a front view of the radiation treatment device of FIG. 1 illustrating travel of a gantry through an arc.
Figure 5:
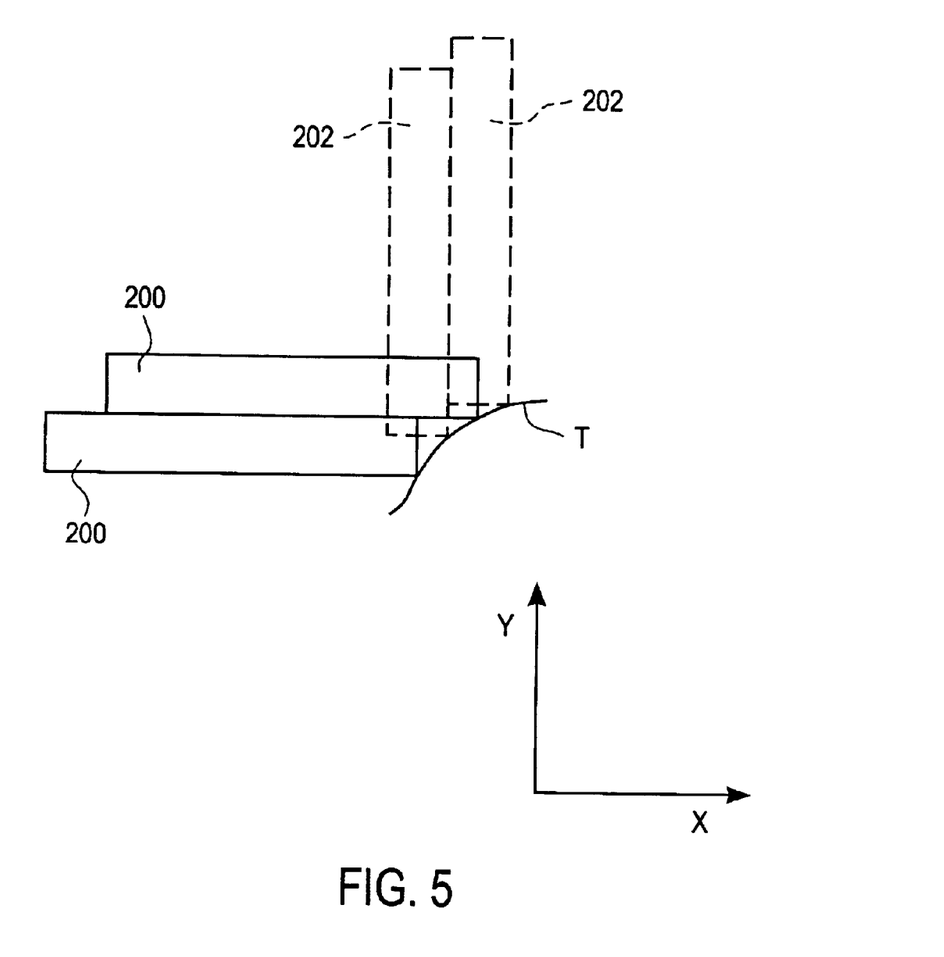
FIG. 5 is a partial plan view showing leaf positions for two separate treatment fields.
Figure 6:
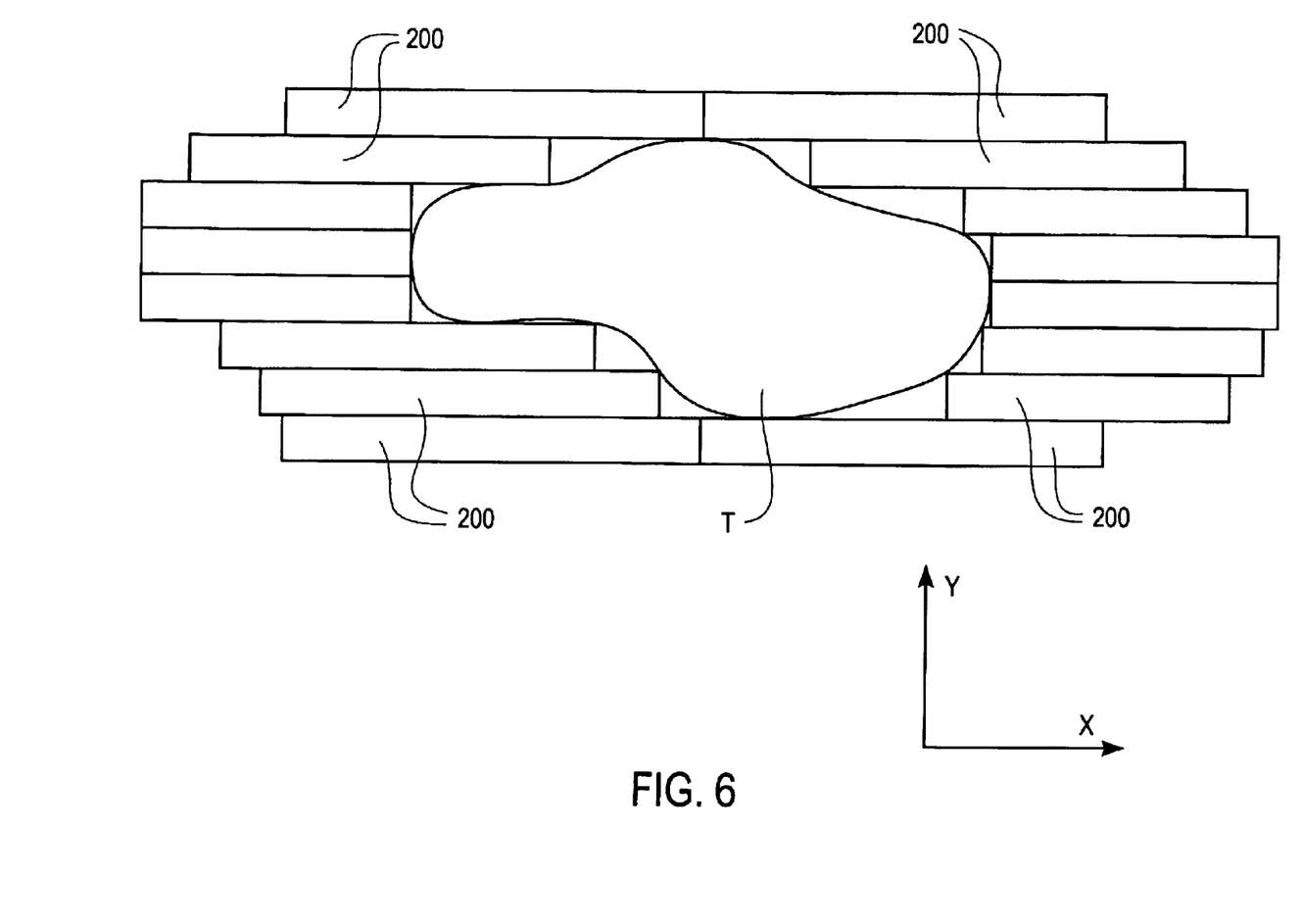
FIG. 6 is a plan view of the multi-leaf collimator positioned in a zero degree offset position.
Figure 7:
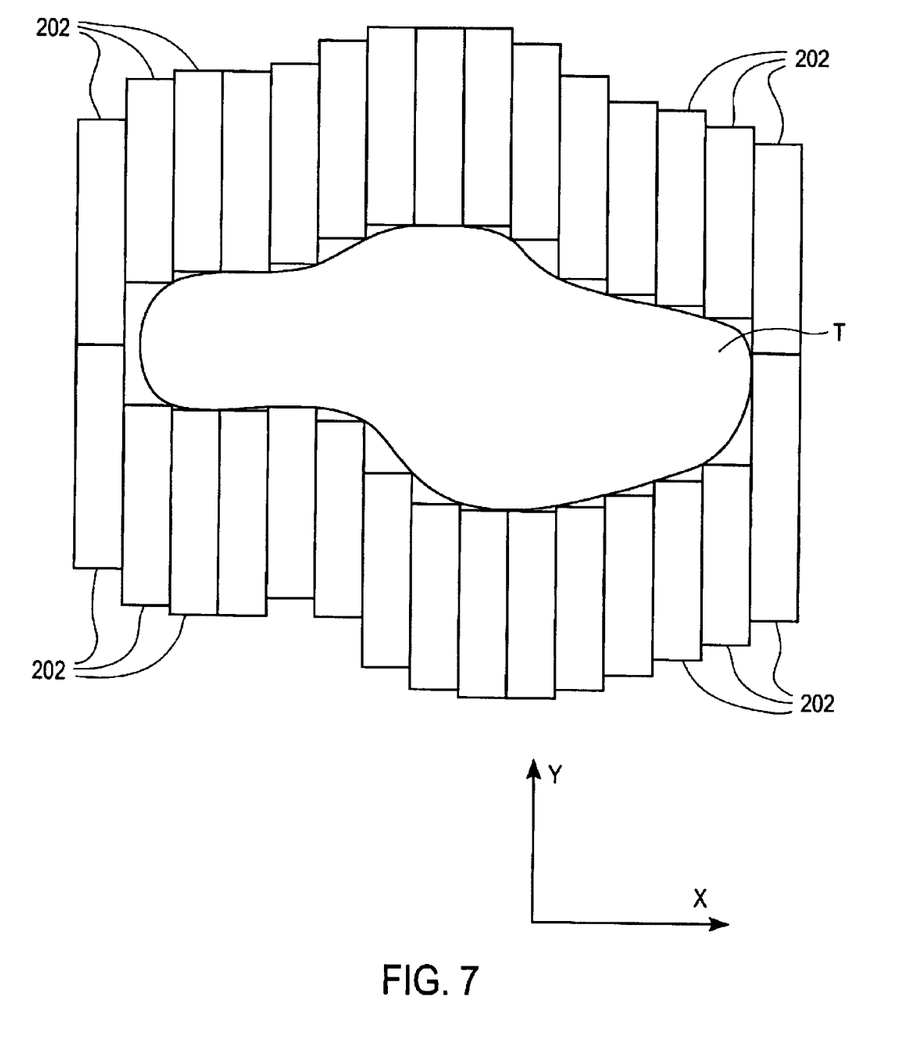
FIG. 7 is a plan view of the multi-leaf collimator of FIG. 6 positioned in a ninety degree offset position.

In arc radiation therapy a contour of a treatment area is shaped by the multi-leaf collimator as the collimator is moved through an arc (FIGS. 1 and 4). The leaves of the collimator preferably remain in a fixed position while the gantry 36 is rotated about axis A. The multi-leaf collimator is also configured for rotation about axis R of the radiation beam, which coincides with a central axis extending perpendicular to a plane containing at least a portion of the leaves (FIG. 1). In order to provide improved resolution and conformation to the contour of the treatment area, the radiation is delivered in at least two separate treatment fields, one with the collimator oriented with the leaves extending longitudinally along an x-axis (FIGS. 5 and 6) and the other with the collimator rotated approximately ninety degrees with the leaves extending along a y-axis (FIGS. 5 and 7). FIG. 5 illustrates a partial plan view of a treatment area T and a portion of the leaves of the multi-leaf collimator positioned in two different collimator orientations to define a border of the treatment area. Leaves 200 extend longitudinally along the x-axis with the collimator in a zero degree offset orientation. Leaves 202 (shown in phantom in FIG. 5) extend longitudinally along the y-axis when the collimator is positioned in a ninety degree offset position. FIG. 5 illustrates that the resolution at the border of the treatment area can be increased by applying the radiation in two different collimator orientations. The leaves 200, 202 may also be moved longitudinally while the collimator remains in its same orientation to further increase the resolution. The number of leaf positions and collimator orientations used in a radiation treatment depend on how fine a resolution or "smooth" a contour is desired. Any number of intensity fields may be used to deliver the radiation at different collimator orientations and various longitudinal leaf positions to provide the desired contour along a periphery edge of the treatment area.

If the radiation is to be delivered through more than two treatment fields the leaves will be repositioned while the collimator is in its zero degree offset position, ninety degree offset position, or both positions. For example, the leaves may be positioned to define a first treatment field with the collimator in its zero degree offset position and the gantry 36 moved through an arc from a first position A to a second position B (FIG. 4). While the gantry 36 is in position B, the leaves are moved longitudinally to slightly increase the area through which the radiation is delivered to define a second treatment field (i.e., opposing leaf pairs are moved away from one another. The position of the leaves relative to the treatment field may be defined as described in U.S. patent application Ser. No. 09/642,553, by A. Siochi, which is incorporated herein by reference, for example. The gantry 36 is then moved from position B to position A, back through the same arc while delivering radiation to the second treatment field. After the gantry has reached position A, the collimator is rotated about axis R (FIG. 1) to its ninety degree offset position. The leaves are then adjusted to define a third treatment field. The gantry 36 moves back through the arc from position A to position B while radiation is delivered through the third treatment field. The leaves may be repositioned (i.e., moved longitudinally) to define a fourth treatment field and the gantry 36 moved once again through the arc while delivering radiation to the fourth treatment field. The gantry 36 preferably moves back and fourth between positions A and B through the same arc, however, the gantry may move through a different arc and move to a different position, without departing from the scope of the invention.

The gantry 36 is rotated through an arc at least once for each treatment field (FIG. 4). If an even number of treatment fields are to be used (e.g., two passes of the gantry through the arc) half of the prescribed dose of radiation is delivered with the leaves extending along the x-axis and the other half of the prescribed dose is delivered with the leaves extending along the y-axis. If an odd number of intensity fields are to be delivered, radiation will be delivered to an additional treatment field with the collimator in either its zero degree offset or ninety degree offset position. The amount of radiation delivered is preferably evenly divided among all of the treatment fields.

Figure 8:
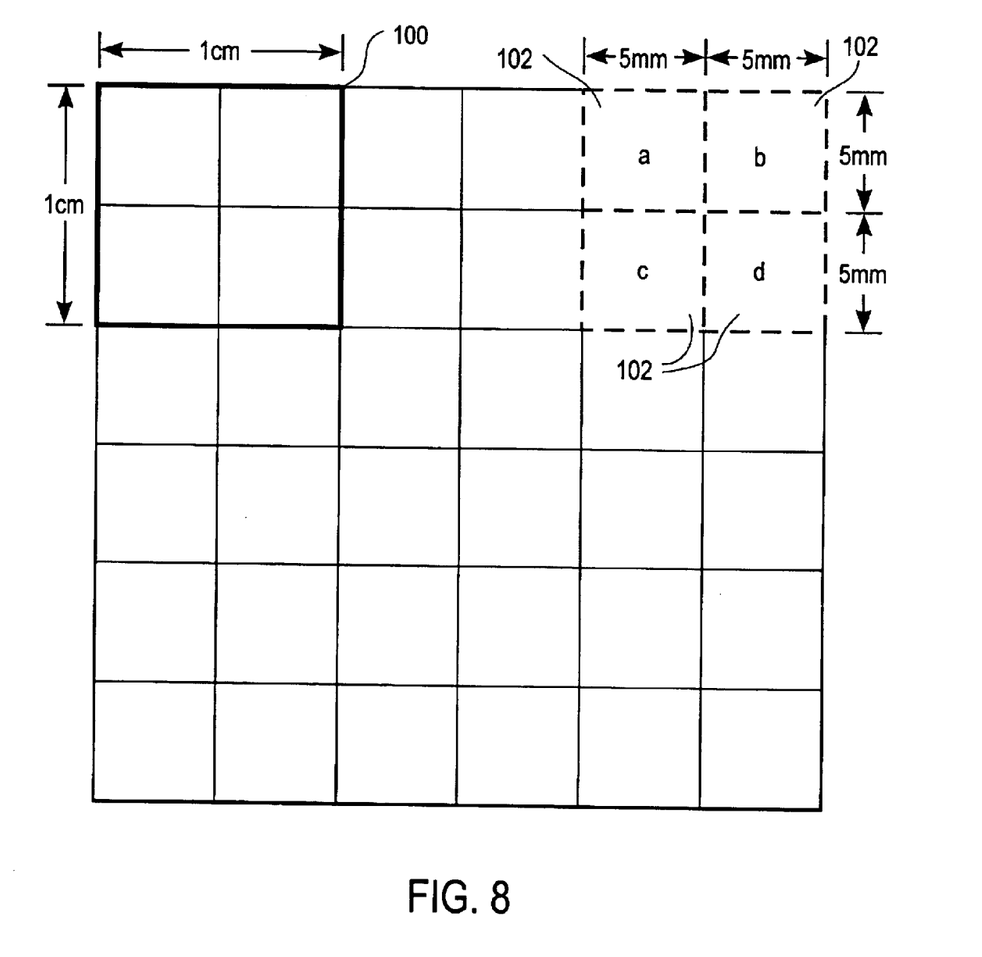
FIG. 8 is a schematic illustrating cells located in an intensity map.

The treatment fields may be defined by developing an intensity map for the treatment area and converting the intensity map into two (or more) orthogonal treatment fields, one for delivery with the collimator in its zero degree position and one for delivery with the collimator in its ninety degree position. FIG. 8 illustrates an intensity map having a plurality of 1 cm×1 cm macrocells 100 (indicated by dark lines) divided into four 5 mm×5 mm microcells 102 (indicated by dashed lines). The 5 mm×5 mm microcells 102 are used to convert macrocell 100 into two orthogonal intensity maps, one with a resolution of 5 mm×10 mm, and the other with a resolution of 10 mm×5 mm. An example of a process for dividing the intensity map into groups of four 5 mm×5 mm microcells 102 is described in U.S. patent application Ser. No. 09/234,364, by Siochi, filed Jan. 20, 1999, which is incorporated herein by reference in its entirety. This grouping of 5 mm×5 mm microcells 102 allows for treatment of a field with a 5 mm×5 mm resolution using a multi-leaf collimator having one centimeter leaves, as shown in FIG. 3.

Figure 9:
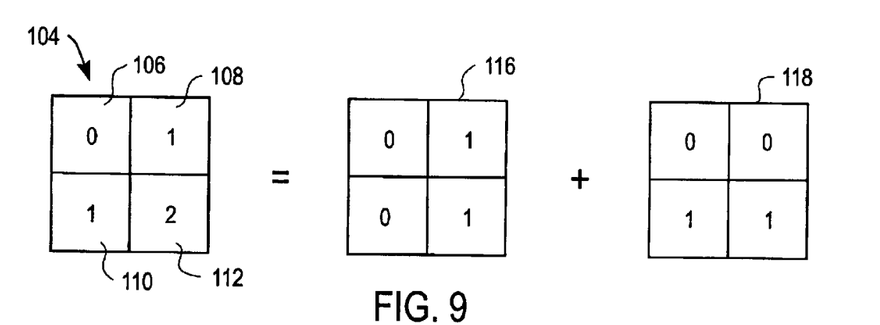
FIG. 9 is a diagram of a matrix broken down into a zero degree matrix component and a ninety degree matrix component.
Figure 10:
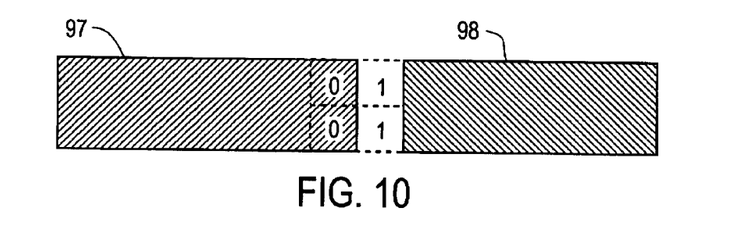
FIG. 10 is a plan view of an opposing pair of leaves configured to apply a dosage specified by the zero degree matrix of FIG. 9.
Figure 11:
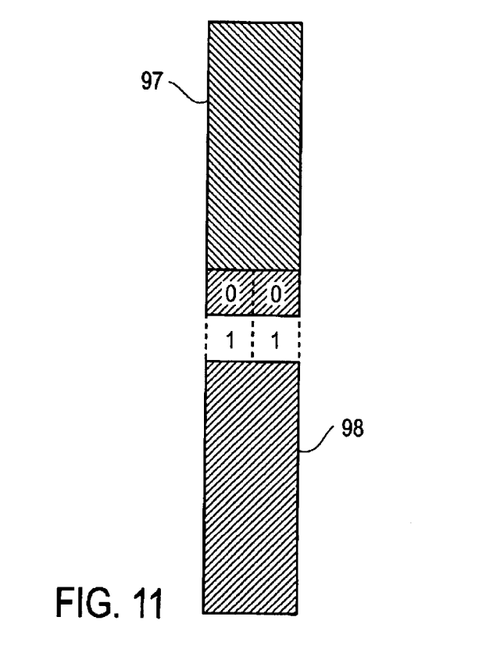
FIG. 11 is a plan view of an opposing pair of leaves configured to apply a dosage specified by the ninety degree matrix of FIG. 9.

FIG. 9 illustrates an example of a matrix, generally indicated at 104 formed from an intensity map composed of four 5 mm×5 mm microcells 106, 108, 110, 112. Each microcell 106, 108, 110, 112 identifies a section in a field to be treated with radiation. The numbers (0, 1, 1, 2) within each microcell 106, 108, 110, 112, respectively, represent the radiation intensity level for locations within the field and are in monitor units (mu) or relative monitor unit intensities (e.g., 1×10² mu). In order to provide 5 mm×5 mm resolution for the intensity map, the matrix 104 is broken down into two orthogonal matrices, 116, 118 having a 1 cm×5 mm resolution and 5 mm×1 cm resolution, respectively. A one centimeter leaf width multi-leaf collimator may then be used to deliver the intensity map with a 5 mm×5 mm resolution. For example, a pair of leaves 97, 98 positioned as shown in FIG. 10 may be used to deliver the intensity map shown in matrix 116 of FIG. 9. A dose of radiation (e.g., 1 mu) is applied to fields corresponding to microcells 108 and 112 of matrix 104. The collimator is then rotated approximately ninety degrees to deliver the intensity map shown in matrix 118 with the leaf position shown in FIG. 11. With the collimator rotated ninety degrees, a dose of radiation (e.g., 1 mu) is applied to the fields corresponding to microcells 110 and 112 of matrix 104. The two radiation applications result in a 2 mu dose to the field corresponding to microcell 112, a 1 mu dose to the fields corresponding to microcells 108 and 110, and no radiation being applied to the field corresponding to microcell 106. The decomposition of the matrix 104 into orthogonal matrices 116 and 118 thus provides for 5 mm×5 mm resolution treatment using collimator leaves having a one centimeter width.

In the following description, the original input intensity map is defined as a macromatrix and the groups of four microcells within the macromatrix are defined as micromatrices (or matrices). In order for the intensity map to be decomposed into orthogonal maps, the vertical gradients of each column of the micromatrix (matrix) 100 must be equal to one another and the horizontal gradients of each row of the micromatrix must also be equal to one another (FIG. 8).

This provides a 1 cm×1 cm area under the intersection of one leaf pair for one collimator setting and another leaf pair for the orthogonal collimator setting. For example, if the horizontal gradients are equal for the micromatrix having cells 102 (shown in FIG. 8) the following equation must apply:

$$b-a=d-c;$$

where: a, b, c, d are the intensity values corresponding to locations in the micromatrix 102 of FIG. 8.

Similarly, if the vertical gradients are equal the following equation must apply:

$$c-a=d-b.$$

A method for converting an intensity map which does not meet the above constraints (i.e., horizontal gradients for each row are not equal or vertical gradients for each column are not equal), in to an intensity map having equal horizontal and vertical gradients is described in U.S. patent application Ser. No. 09/457,601, filed Dec. 8, 1999, which is incorporated herein by reference. Several decompositions of an intensity map are possible to create the two orthogonal maps. An optimization method such as described in U.S. patent application Ser. No. 09/457,602, filed Dec. 8, 1999, which is incorporated herein by reference, may be used to find the decompositions which yields the shortest treatment time to minimize overall treatment time and increase the life of the radiation treatment device.

The intensity map may be broken down into microcells having a dimension other than 5 mm×5 mm if a different resolution is required. For example, each macrocell may be divided into nine microcells in which case the intensity map may be deliverable as two orthogonal intensity maps having a resolution of 1 cm×⅓ cm and ⅓ cm×1 cm (see, for example, U.S. patent application Ser. No. 09/234,364, referenced above). Also, a multi-leaf collimator having leaves with a width other than 1 cm may be used, and the size of the corresponding microcells will be 1/n times the leaf width (where n is a positive integer (e.g., 2 or 3).

Figure 12:
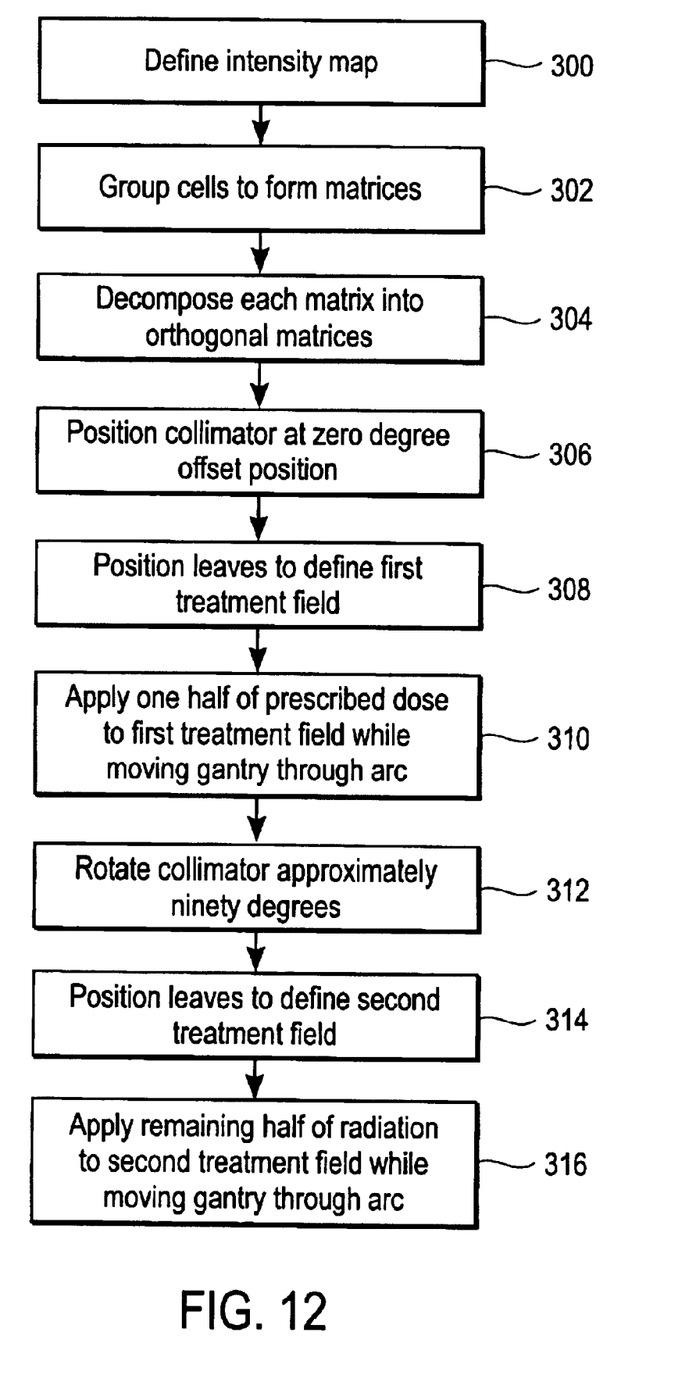
FIG. 12 is a flowchart illustrating a process for delivering conformal arc radiation therapy with a multi-leaf collimator.

FIG. 12 is a flowchart illustrating a process for delivering conformal arc radiation therapy with a multi-leaf collimator. At step 300 the intensity map is first defined for the treatment area T. The cells are then grouped to form matrices (step 302). At step 303 matrices arc filtered as described in U.S. patent application Ser. No. 09/457,601. Each matrix is decomposed into orthogonal matrices (step 304). The collimator is first positioned in its zero degree offset orientation (step 306). The leaves are positioned to define the first treatment field (step 308) and the radiation is delivered through the first treatment field as the collimator is moved through an arc over the treatment area (step 310). After the radiation is delivered for the first treatment field, the collimator is rotated approximately ninety degrees about the beam axis R (step 312). The leaves are then moved longitudinally to define a second treatment field (step 314) and the collimator is moved back through the arc while delivering radiation through the second treatment field (step 316). The leaves may also be repositioned before changing the orientation of the collimator to define additional treatment fields. The sequence of delivery of the treatment fields may also be modified to reduce the amount of travel of the leaves.

Although present invention has been described in accordance with the embodiments shown, one of ordinary skill in the art will readily recognize that there could be variations made to the embodiments without departing from the scope of the present invention. Accordingly, it is intended that all matter contained in the above description and shown in the accompanying drawings shall be interpreted as illustrative and not in a limiting sense.

What is claimed is:

1. A method for delivering radiation from a radiation source to treatment area, comprising:
   positioning a multi-leaf collimator between the radiation source and the treatment area to block a portion of the radiation and define a first treatment field, the collimator being positioned with leaves of the collimator extending longitudinally in a first direction;
   moving the multi-leaf collimator through a first arc over the treatment area while delivering radiation through the first treatment field to the treatment area;
   rotating the multi-leaf collimator about a central axis extending generally perpendicular to a plane containing at least a portion of the leaves such that the leaves define a second treatment field; and
   moving the multi-leaf collimator through a second arc over the treatment area while delivering radiation through the second treatment field to the treatment area.

2. The method of claim 1 wherein moving the multi-leaf collimator through a first arc comprises moving the collimator from a first position to a second position and moving the multi-leaf collimator through a second arc comprises rotating the collimator from the second position to the first position.

3. The method of claim 1 wherein the first arc has the same geometry as the second arc.

4. The method of claim 1 wherein the first arc has the same starting and ending points.

5. The method of claim 1 further comprising moving the leaves longitudinally after moving the multi-leaf collimator through the first arc to define a third treatment field and moving the multi-leaf collimator back through the first arc in an opposite direction while delivering radiation through the third treatment field.

6. The method of claim 5 wherein moving the leaves longitudinally comprises moving the opposing pairs of leaves away from one another.

7. The method of claim 1 wherein rotating the multi-leaf collimator comprises rotating the collimator until leaves extend longitudinally in a second direction generally orthogonal to said first direction.

8. The method of claim 1 wherein delivering radiation through said first treatment field comprises delivering on half of a prescribed radiation dose and delivering radiation to said second treatment field comprises delivering a remaining half of the prescribed radiation dose.

9. A method for delivering radiation from a radiation source to a treatment area, comprising:
   dividing said treatment area into a plurality of cells each having a defined treatment intensity level;
   grouping the cells to form a plurality of matrices, each of the matrices having at least one dimension approximately equal to a width of the collimator leaf;
   decomposing each of the matrices into orthogonal matrices to identify a plurality of treatment fields;
   positioning a multi-leaf collimator between the radiation source and the treatment area to block a portion of the radiation and define a first treatment field, the collimator being positioned with leaves of the collimator extending longitudinally in a first direction;
   moving the multi-leaf collimator through a first arc over the treatment area while delivering radiation through the first treatment field to the treatment area;
   rotating the multi-leaf collimator about a central axis extending generally perpendicular to a plane containing at least a portion of the leaves such that the leaves define a second treatment field; and
   moving the multi-leaf collimator through a second arc over the treatment area while delivering radiation through the second treatment filed to the treatment area.

10. The method of claim 9 wherein radiation is delivered with a resolution on half times the leaf width.

11. The method of claim 9 wherein the collimator leaves have a width of 1 cm and the cells are approximately 1 cm×5 mm.

12. A method for delivering radiation from a radiation source to a treatment area, comprising:
    dividing said treatment area into a plurality of cells, each having a defined treatment intensity level, and grouping the cells to form a plurality of matrices defining treatment fields;
    positioning a multi-leaf collimator between the radiation source and the treatment area to block a portion of the radiation and create a first treatment field defined by a least one of said plurality of matrices, the collimator being positioned with leaves of the collimator extending longitudinally in a first direction;
    moving the multi-leaf collimator through a first arc over the treatment area while delivering radiation through the first treatment field to the treatment area;
    rotating the multi-leaf collimator about a central axis extending generally perpendicular to a plane containing at least a portion of the leaves such that the leaves define a second treatment field defined by at least one of said plurality of matrices; and
    moving the multi-leaf collimator through a second arc over the treatment area while delivering radiation through the second treatment field to the treatment area.

13. A system for delivering radiation from a radiation source to a treatment area comprising:
    a collimator having multiple leaves for blocking radiation from said source and defining an opening between the radiation source and said treatment area, the collimator operable to move through an arc over said treatment area and rotate about a central axis of a radiation beam emitted from said radiation source; and
    a controller configured to position the leaves to define a first treatment field, move the collimator through a first arc while delivering radiation through the first treatment field, rotate the collimator about the central axis, position the leaves to define a second treatment field, and move the collimator through a second arc while delivering radiation through the second treatment field to the treatment area.

14. The system of claim 13 further comprising a processor configured to divide said treatment area into a plurality of cells each having a defined treatment intensity level, group the cells to form a plurality of matrices, and decompose each of the matrices into orthogonal matrices to identify a plurality of treatment fields.

15. The system of claim 14 wherein each of the matrices has at least one dimension approximately equal to a width of the collimator leaf.

* * * * *